United States Patent [19]

Aida et al.

[11] Patent Number: 4,558,709
[45] Date of Patent: Dec. 17, 1985

[54] GAS INTRODUCING APPARATUS FOR RESPIRATORY GAS ANALYZER

[75] Inventors: Satoshi Aida; Ayao Itoh, both of Yokohama, Japan

[73] Assignee: Tokyo Shibaura Denki Kabushiki Kaisha, Kawasaki, Japan

[21] Appl. No.: 545,155

[22] Filed: Oct. 25, 1983

[30] Foreign Application Priority Data

Oct. 30, 1982 [JP] Japan .................. 57-191443
Nov. 2, 1982 [JP] Japan .................. 57-191912

[51] Int. Cl.[4] ............................................. A61B 5/08
[52] U.S. Cl. .................................. 128/719; 73/863.23
[58] Field of Search ............. 128/719, 730, 716, 717, 128/718, 765, 204.22, 201.23, 201.25, 201.27, 201.28, 201.29, 205.12, 204.18, 205.26; 604/246; 73/863.23, 863.86

[56] References Cited

U.S. PATENT DOCUMENTS

| 2,515,470 | 7/1958 | Prytz ........................ 604/246 |
| 2,986,939 | 6/1961 | Gould ........................ 73/863.86 |
| 3,933,652 | 1/1976 | Weichselbaum et al. ...... 210/510.1 |
| 4,456,014 | 6/1984 | Buck et al. ................. 128/719 |

OTHER PUBLICATIONS

Iyo Denshi to Seitai Kogaku (Medicinal Electrons & Biological Engineering) pp. 282–283, Mass Spectrometer Applied to Medicine by Masahiro Kusakabe et al, 1980, 5,8.

Primary Examiner—Henry J. Recla
Attorney, Agent, or Firm—Oblon, Fisher, Spivak, McClelland & Maier

[57] ABSTRACT

A gas introducing apparatus for a respiratory gas analyzer which comprises a gas introducing tube for guiding sampled gas from an airway tube inserted into the airway of a patient to a gas analyzer, and a sintered metal filter hermetically and detouchably mounted on a distal end of the gas introducing tube.

8 Claims, 7 Drawing Figures

GAS INTRODUCING APPARATUS FOR RESPIRATORY GAS ANALYZER

BACKGROUND OF THE INVENTION (a) Field of the Invention

The present invention relates to a gas introducing apparatus for sampling from an airway tube a gas to be measured into a respiratory gas analyzer.

(b) Description of the Prior Art

Collection of the respiratory gas and analysis of its components are performed to monitor the gaseous metabolism of a patient. In this case, a gas introducing tube with a filter at its distal end for filtering out foreign materials such as chemicals, dust, or water contained in the respiratory gas is used as a means for introducing a gas sampled from a patient into a gas analizer.

As shown in FIG. 1, a gas introducing tube 5 is connected through a connector 4 to a junction between an airway tube 2 inserted into the airway of a patient and an artificial respirator 3. Part of the respiratory gas of the patient is introduced into a gas analyzer 6 through the gas introducing tube 5.

FIG. 2 shows a typical structure of a conventional gas introducing tube with a filter. A fibrous, porous membrane filter 12 is mounted at the distal end of a resin tube body 11. Although the membrane filter 12 permeates gases well it has a poor mechanical strength. In view of this problem, a shaping spring 13 for supporting the filter 12 is placed therein such that the filter 12 is connected to the tube body 11 through the spring 13. This reduces the effective area of gas sampling and results in a complex assembly process. A membrane filter of this type has low thermal and chemical resistance and therefore presents problems in ensuring sterility.

In addition to this, in a membrane filter of the structure as described above, the filter itself has a poor mechanical strength. When such a filter is detachably connected to a gas introducing tube, the possibility of accidental removal of the filter from the tube presents a large threat to the safety of the patient. For this reason, it is extremely difficult to detachably mount the filter on the tube. Accordingly, when a filter securely and integrally fixed to a gas introducing tube becomes clogged, the entire filter/gas introducing tube assembly must be entirely replaced with a new assembly. This requires extra cost and replacement work.

SUMMARY OF THE INVENTION

It is an object of the present invention to provide a gas introducing apparatus for a respiratory gas analyzer, which is improved over a conventional gas introducing tube, which has good mechanical, thermal and chemical resistance and can take any shape, and which has a filter mechanism which can be detachably mounted on a gas introducing tube.

According to an aspect of the present invention, there is provided a gas introducing apparatus for a respiratory gas analyzer, having a gas introducing tube for introducing a gas sampled from a patient to the gas analyzer, and a filter hermetically mounted at a distal end of said tube, characterized in that the filter comprises a metal filter made preferably of a sintered metal powder.

DETAILED DESCRIPTION OF THE PREFERRED EMBODIMENTS

Figure 3:
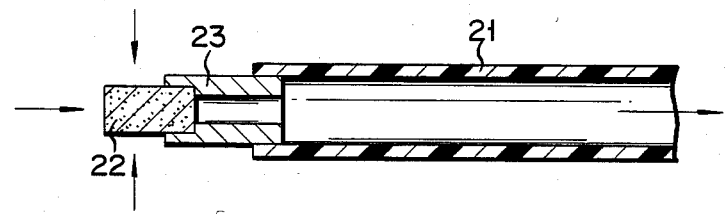
FIG. 3 is a sectional view of a gas introducing apparatus according to an embodiment of the present invention.

FIG. 3 shows a gas introducing apparatus according to an embodiment of the present invention. Referring to FIG. 3, reference numeral 21 denotes a gas introducing tube for introducing a gas sampled from a patient into a gas analyzer. The gas introducing tube 21 consists of, for example, a fluorine resin or the like. A columnar metal filter 22 obtained by sintering a metal powder is mounted at the distal end of the gas introducing tube 21 through a metal mounting cylinder 23.

The metal used for the metal filter 22 is selected from those metals which have good chemical, thermal and mechanical resistance, since the filter may be exposed to such kinds of wear. Stainless steel, for example, selected from such metals, is pulverized into a powder having a particle size of several to several hundred micrometers. The powder is sintered at a predetermined temperature to provide the metal filter 22. The metal mounting cylinder 23 is similarly made from a metal which has good chemical, thermal and mechanical resistance.

Referring to FIG. 3, one end of the metal mounting cylinder 23 is inserted into the distal end of the gas introducing tube 21. The proximal end of the filter 22 is inserted into the other end of the metal mounting cylinder 23. However, the type of connection between the filter 22 and the cylinder 23 or between the cylinder 23 and the tube 21 may be freely selected. For example, the tube 21 and the cylinder 23 may be adhered together with an adhesive; alternatively they may be hermetically held in position by a separate external member. The filter 22 and the cylinder 23 may be coupled by welding or may be coupled strongly and hermetically by other coupling means such as screws. In a gas introducing apparatus having the above construction, the filter 22 and the cylinder 23 have good mechanical strength. For this reason, the filter 22 and the cylinder 23 are resistant to internal or external impact or pressure, and are easy to manufacture.

Figure 4:
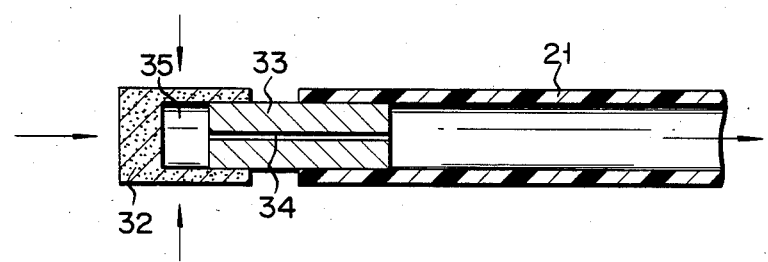
FIGS. 4 and 5 are sectional views respectively showing gas introducing apparatuses according to other embodiments of the present invention.

In the embodiment shown in FIG. 4, a metal mounting cylinder 33 for connecting a gas introducing tube 21 and a metal filter 32 has a thin hole (capillary hole) 34 at its center. One end of the cylinder 33 is inserted into the distal end of the tube 21. The other end of the cylinder 33 is fitted into the partially hollow filter 32 so as to define an internal space 35 therein. The tube 21, the filter 32 and the cylinder 33 may consist of similar materials to those used in the embodiment shown in FIG. 3. The capillary hole 34 communicates the space 35 with the interior of the tube 21. The capillary hole 34 has an inner diameter of 0.1 to 0.5 mm and has a constant conductance to various sampled gases which may be passed therethrough. The inner diameter of the capillary hole 34 may be freely selected such that the balance between the gas introducing amount and a response time required for the gas to reach a gas analyzer may be optimal.

The capillary hole 34 may be omitted. In this case, a similar effect to that obtainable with the capillary hole 34 can be obtained by properly selecting a particle size of a metal powder of the filter so as to lessen the conductance.

Figure 5:
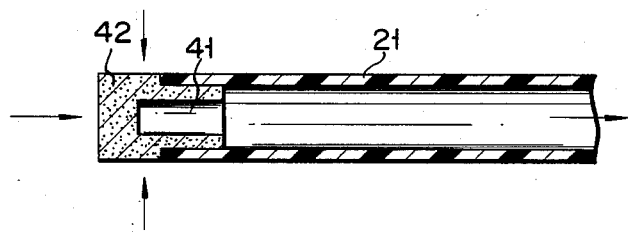

In the embodiment shown in FIG. 5, a metal filter 42 is molded into the form of a stopper (an inner recess 41 is formed). The metal filter 42 is directly coupled to a gas introducing tube 21. The material of the metal filter 42 can be the same as in the case of the embodiment shown in FIG. 3. In this case, the filter 42 and the tube 21 can be securely fixed through an adhesive or by an external clamping member.

Figure 6:
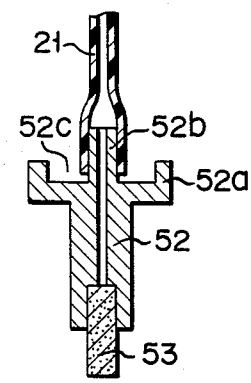
FIG. 6 is a sectional view of a gas introducing apparatus according to still another embodiment of the present invention.

In the embodiment shown in FIG. 6, a metal mounting cylinder 52 connects a gas introducing tube 21 and a columnar metal filter 53. The metal filter 53 is connected to the distal end of the cylinder 52 by welding or the like. The cylinder 52 has a collar 52a at its proximal end, and a thin tubular projection 52b to be inserted into the tube 21 at its center, an annular groove 52c being defined between the outer surface of the projection 52b (including that of the tube 21) and the top surface of the collar 52a. The annular groove 52c receives one end of a clmaping metal piece, to be described later.

Figure 1:
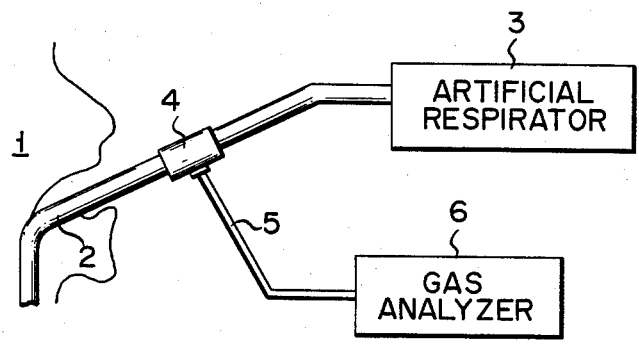
FIG. 1 is a schematic view of a gas introducing apparatus in the state wherein it is in use.
Figure 2:
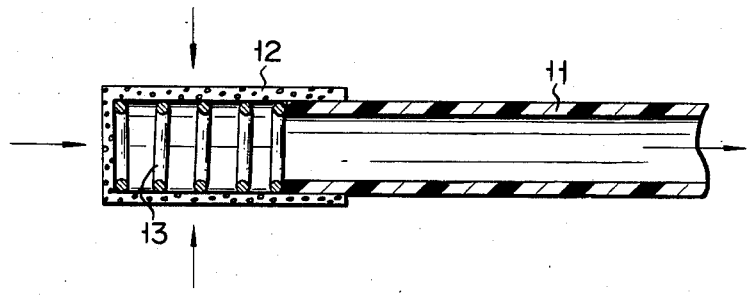
FIG. 2 is a sectional view of an example of a conventional gas introducing apparatus.
Figure 7:
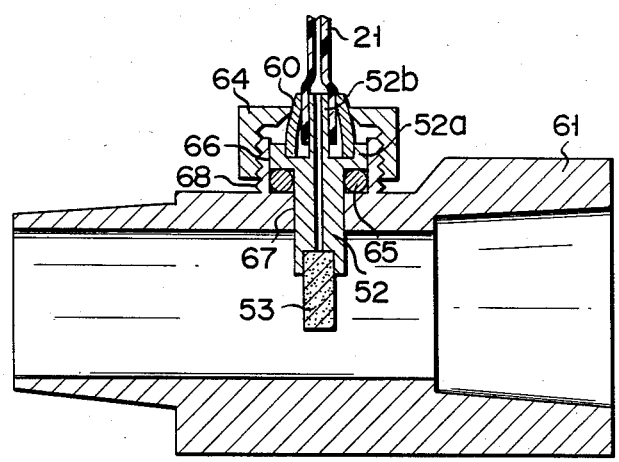
FIG. 7 is a sectional view showing the gas introducing apparatus shown in FIG. 6 in the state wherein it is mounted to a connector.

The gas introducing apparatus having the above construction is mounted on a connector 61 as shown in FIG. 7. In the manner as shown in FIG. 1, the connector 61 is coupled between an artificial respirator and an airway tube. The connector 61 has at its side surface a cylindrical housing 66 having outer threads 68 for receiving the proximal end of the cylinder 52. A hole 67 for receiving the distal end of the filter 53 for insertion into the connector 61 is formed at the center of the housing 61.

An O-ring 65 is mounted between the lower surface of the collar 52a of the cylinder 52 and the connector side surface. A clamping metal piece 60 is received in the annular groove 52c. A cap nut 64 is located so as to completely connect the gas introducing tube 21 and the projection 52b at the upper end of the metal piece 60. At the same time, the lower end of the metal piece 60 urges against the O-ring 65 so as to provide a good hermetic seal between the cylinder 21 and the interior of the connector 61. With an apparatus of such a structure, the cylinder 52 and the filter 53 are not involved in the respiratory circuit, and the tube 21 and the cylinder 52 can be detachably connected.

When the amount of sampled gas is decreased due to clogging of the filter 53, the cap nut 64, the metal piece 60, the gas introducing tube 21, and the O-ring 65 are removed. Then, only the assembly of the cylinder 52 and the filter 53 need be replaced with a new assembly. Thus, the tube 21 can be used again.

According to the present invention, the filter is not a fibrous filter as in the conventional cases but is a metal sintered body. For this reason, the filter of the present invention has an improved mechanical strength. The filter may also have any desired shape within the limitations imposed by processing precision, and a shaping guard such as a spring or the like need not be used.

Furthermore, since the filter of the present invention has improved chemical and thermal resistance, it can be sterilized by various chemicals or by boiling, which has hitherto been impossible. If the particle size of a metal powder of the filter is properly selected, a filter having a suitable conductance can be manufactured.

A metal mounting cylinder consisting of a metal of the same type can be sintered or welded to the filter. The filter is hard and has a high mechanical strength. Accordingly, the filter can be easily and reliably mounted on a gas introducing tube, providing ease in manufacture of gas introducing apparatuses.

With a conventional gas introducing apparatus, when a metal mounting cylinder or a filter become damaged or clogged, respectively, a tube for supplying a gas sampled from a patient to a gas analyzer, the filter, and the cylinder must all be replaced. However, this is not the case according to the present invention. According to a gas introducing apparatus of the present invention, only the filter and the metal mounting cylinder are removed from the tube and are replaced. Thus, time for maintenance of the apparatus is shortened, and the tube requires only infrequent replacement.

What is claimed is:

1. A gas introducing apparatus for a respiratory gas analyzer, comprising:
   a metal filter disposed in a respiratory gas flow passage for filtering and sampling the respiratory gas, said metal filter being made of sintered metal powders; and
   a gas introducing tube, a distal end of which is hermetically connected with said metal filter, for guiding a sampled gas to said gas analyzer.

2. An apparatus according to claim 1, including a metal mounting cylinder fixed to said filter and mounting said filter to said gas introducing tube.

3. An apparatus according to claim 2, wherein said metal mounting cylinder is detachably mounted on said gas introducing tube.

4. An apparatus according to claim 1, wherein said metal filter is obtained by sintering a metal powder having a particle size of several to several hundreds of micrometers.

5. An apparatus according to claim 1, wherein said metal filter consists of stainless steel.

6. An apparatus according to claim 1, wherein said metal filter is detachably mounted on said gas introducing tube.

7. A gas introducing apparatus for a respiratory gas analyzer, comprising:
   a metal filter disposed in a respiratory gas flow passage for filtering and sampling the respiratory gas, said metal filter being made of sintered metal powders;
   a metal mounting cylinder having an inner diameter of 0.12 to 0.5 mm, one end of which is fixed to said metal filter; and
   a gas introducing tube, a distal end of which is hermetically connected with another end of said mounting cylinder for guiding a sampled gas through said metal filter to said gas analyzer.

8. A gas introducing apparatus for a respiratory gas analyzer, comprising:
   a metal filter disposed in a respiratory gas flow passage for filtering and sampling the respiratory gas, said metal filter being made of sintered metal powders;

a metal mounting cylinder having a distal end fixed to said metal filter and a proximal end;

a gas introducing tube, a distal end of which is hermetically and detachably connected with said proximal end of said mounting cylinder for guiding a sampled gas through said metal filter to said gas analyzer;

a clamping means clamping said gas introducing tube to said metal mounting cylinder; and an O-ring provided around an outer wall of said metal mounting cylinder for preventing said respiratory gas flow from leaking through the outer wall of said metal mounting cylinder.

* * * * *